(12) United States Patent
Mouton

(10) Patent No.: US 10,682,434 B2
(45) Date of Patent: Jun. 16, 2020

(54) WOUND DRESSING

(71) Applicant: Jacobus Frederick Mouton, Pretoria (ZA)

(72) Inventor: Jacobus Frederick Mouton, Pretoria (ZA)

( * ) Notice: Subject to any disclaimer, the term of this patent is extended or adjusted under 35 U.S.C. 154(b) by 447 days.

(21) Appl. No.: 15/528,895

(22) PCT Filed: Nov. 24, 2015

(86) PCT No.: PCT/ZA2015/050026
§ 371 (c)(1),
(2) Date: May 23, 2017

(87) PCT Pub. No.: WO2016/086243
PCT Pub. Date: Jun. 2, 2016

(65) Prior Publication Data
US 2017/0326267 A1    Nov. 16, 2017

(30) Foreign Application Priority Data
Nov. 24, 2014  (GB) .................................. 1420862.3

(51) Int. Cl.
| | |
|---|---|
| *A61L 15/46* | (2006.01) |
| *D04H 1/4258* | (2012.01) |
| *D04H 1/4266* | (2012.01) |
| *D04H 1/435* | (2012.01) |
| *A61F 13/00* | (2006.01) |
| *D04H 1/4382* | (2012.01) |
| *D04H 1/46* | (2012.01) |
| *D04H 1/498* | (2012.01) |
| *A61L 15/28* | (2006.01) |

(52) U.S. Cl.
CPC ........ *A61L 15/46* (2013.01); *A61F 13/00008* (2013.01); *A61F 13/00063* (2013.01); *A61L 15/28* (2013.01); *D04H 1/4258* (2013.01); *D04H 1/4266* (2013.01); *D04H 1/435* (2013.01); *D04H 1/4382* (2013.01); *D04H 1/46* (2013.01); *D04H 1/498* (2013.01); *A61F 13/00042* (2013.01); *A61L 2300/404* (2013.01)

(58) Field of Classification Search
CPC ..... A61L 15/46; A61L 15/28; A61F 13/00063
See application file for complete search history.

(56) References Cited

U.S. PATENT DOCUMENTS

| | | | | |
|---|---|---|---|---|
| 2002/0168911 | A1* | 11/2002 | Tonner .............. | A61F 13/00042 442/405 |
| 2011/0280926 | A1* | 11/2011 | Junginger ......... | A61F 13/00991 424/445 |
| 2012/0115729 | A1* | 5/2012 | Qin ...................... | C08K 5/3445 504/358 |

FOREIGN PATENT DOCUMENTS

| | | | |
|---|---|---|---|
| CN | 103655046 | * | 3/2014 |
| EP | 1 035 817 B1 | | 6/2002 |
| JP | 2003-144116 | * | 5/2003 |
| WO | WO 2007/085884 A1 | | 8/2007 |
| WO | WO 2011/138771 A2 | | 11/2011 |

OTHER PUBLICATIONS

Japanese Notice of Reasons for Refusal (Year: 2019).*
European Search Report (Year: 2018).*
English Translation of Description, CN103655046 (Year: 2014).*
English Translation of Description, JP2003-144116 (Year: 2003).*
International Search Report for Application No. PCT/ZA2015/050026 dated Apr. 22, 2016, 4 pages.

\* cited by examiner

*Primary Examiner* — Ariana Zimbouski
(74) *Attorney, Agent, or Firm* — Howard & Howard Attorneys PLLC

(57) ABSTRACT

The invention provides a wound dressing, which includes a 1 to 12 mm thick layer of absorbent non-woven fibre material between 150 and 1200 grams per square meter, which layer includes a mixture of viscose fibres and polyester fibres which more viscose than polyester, and of which the fines of the viscose is between 1.5 and 3 dtex and the fines of the polyester is between 2 and 3 dtex.

12 Claims, No Drawings

WOUND DRESSING

CROSS-REFERENCE TO RELATED APPLICATIONS

This application is the National Stage of International Patent Application No. PCT/ZA2015/050026, filed on Nov. 24, 2015, which claims priority to and all the advantages of G.B. Patent Application No. 1420862.3, filed on Nov. 24, 2014, the content of which is incorporated herein by reference.

TECHNICAL FIELD OF THE INVENTION

This invention relates to wound dressings.

BACKGROUND TO THE INVENTION

The inventor is aware of the need for a wound dressing, which not only cover and protect the wound but create a healthy wound bed that is well vascularised. The reconstruction of the wound bed is of utmost importance. By this the inventor means to remove barriers and obstructions that prevent or delays wound healing.

Healing is optimized if the wound bed is healthy. It is therefore an object of the invention to provide a dressing which assists the body with the healing process, by preparing the wound bed for healing. An absorbent dressing is very important to absorb body fluid and keep it away from the wound bed, preventing maceration and over granulation.

Breaking down of slough and necrotic tissue improves wound healing, but also increases the volumes of exudates. This must be monitored carefully to prevent damage to healthy skin. Preferably, the dressing materials should also assist with the draining of oedem from the wound bed which reduces swelling and improves blood supply to the wound bed.

It is an object of the invention to provide a highly absorbent wound dressing, which actively assists with the healing process of a wound, in use.

GENERAL DESCRIPTION OF THE INVENTION

According to the invention there is provided a wound dressing, which includes a 1 to 12 mm thick layer of absorbent non-woven fibre material of between 150 and 1200 grams per square meter, which layer includes a mixture of viscose fibres and polyester fibres with more viscose than polyester, and of which the linear density of the viscose is between 1.5 and 3 decitex (dtex) and the linear density of the polyester is between 2 and 3 dtex. Dtex is grams per 10,000 meters of fibre.

The layer of absorbent non-woven fibre material may comprise two or more thinner layers of absorbent non-woven material needle punched together to form the single layer.

The absorbent layer may preferably also include between 7 and 25% chitin fibres mixed or interwoven with the viscose and polyester fibres with the chitin fibres having a linear density between 1.5 and 2.5 dtex.

One or both sides of the layer of absorbent material may be covered by a non-adherent layer. The non-adherent layer or layers may be heat bonded/laminated to the absorbent layer. The non-adherent layer may be a thin film of polyurethane or a HDPE based material such as CM18 produced by Smith & Nephew.

The composite density may be between 150 and 1200 grams per square meter (gsm), preferably about 700-750 gsm.

The polyester fibre length may be between about 30 and 70 mm, preferably about 50 mm.

The viscose fibre length may be between about 20 and 60 mm, preferably about 40 mm.

The chitin fibre length may be between about 30 and 70 mm, preferably about 60 mm.

In the case where two layers are needle punched together to form one layer, the punching density may be between 250 and to 380 punches per square centimetre, preferably about 320.

The construction of the dressing makes the material "super absorbent" with a "pass-on" effect from one dressing to another. The composition of the dressing also secures the exudates inside the dressing without "fall back" or "dripping" of exudates back onto the wound bed. This prevents the damaging of healthy surrounding skin. This dressing helps to reduce swelling and the restoration of the bacterial balance in the deeper compartments of the wound bed. This "pass-on" effect prevents colonization and duplication of bacteria. The antimicrobial fiber that forms part of the composition is very important in controlling bacterial levels on the wound bed, which helps to keep the wound bed healthy.

Some embodiments of the dressing also has a non-adherent film layer that help to protect the healthy wound bed. This film dressing is suitable on all type of wounds especially burns. Superficial healthy wounds with low volumes of exudates may be dressed with the film layer dressing. The film layer does not interfere with the healing process but rather protects the wound bed from any adherence by the dressing. New granulation tissue will not be harmed or damaged. The film may preferably breathable and of HDPE or polyurethane.

DETAILED DESCRIPTION OF THE INVENTION

The invention is now described by way of examples.

Examples 1 and 2, with about 10× by weight absorbency capacity, in accordance with the invention, is a wound dressing, which includes a ±3-5 mm thick layer of absorbent non-woven fibre material of ±700-750 grams per square meter, which layer includes a mixture of 70% viscose fibres and 30% polyester fibres.

Product Specification:

|  | Example 1 | Example 2 |
| --- | --- | --- |
| Polyester Fiber Length 涤纶纤维长度 | 51 mm | 51 mm |
| Vicose Fiber Length 粘胶纤维长度 | 38 mm | 38 mm |
| Polyester Linear density 涤纶密度 | 2.2 dtex | 2.2 dtex |
| Viscose Linear density 粘胶密度 | 1.67 dtex | 1.67 dtex |
| Chitin Fiber Length | X | 60 mm |
| Chitin Fiber Linear density | X | 2 dtex |
| Batt Composition 组成比例 | 70% Viscose 30% Polyester | 60% Viscose 30% Polyester 10% Chitin |
| Punching Density 针刺密度 | 300-350 | 300-350 |
| Composite Mass per Square Meter 混合物重量 | 750 gsm | 750 gsm |
| Composite Thickness 混合物厚度 | 5 mm | 5 mm |

Example 3, with about 10× by weight absorbency capacity, according to the invention there is provided a wound dressing, which includes the absorbent layer of the wound dressing described in Examples 1 and 2, which includes a non-adherent layer on both sides of the layer of absorbent material. The non-adherent layers are heat bonded/laminated to the absorbent layer.

Example 4 includes two absorbent layers which are needle punched together to form one thick absorbent layer as described in Examples 1 and 2.

Example 5 includes the absorbent layer as described in Example 4, which includes a non-adherent layer on both sides of the layer of absorbent material. The non-adherent layers are heat bonded/laminated to the absorbent layer.

Examples 6 to 9 is similar to and corresponds with examples 1 to 4 wherein the viscose is 55%, the polyester is 35% and includes 10% chitin fibres.

Further examples include a wound dressing similar to examples 1 to 9 with the single layer being 200 gsm and about 1 mm thick or being 600 gsm and about 3 mm thick.

The applicant has found that the wound dressing absorbs fluids about 10× its own weight by means of adhesion and cohesion forces as well as electrostatic forces to draw out of the wound solid wound material and fluids vertically and to spread it horizontally in the absorbent layer. The wound material includes harmful bacteria. The wound dressing actively and continuously removes unwanted material from the wound until absorbent capacity is reached keeping the wound clear allowing the wound to heal faster than without the wound dressing. In addition, the chitin fibres also provide an antimicrobial function.

It shall be understood that the examples are provided for illustrating the invention further and to assist a person skilled in the art with understanding the invention and are not meant to be construed as unduly limiting the reasonable scope of the invention.

The invention claimed is:

1. A wound dressing, which includes a 1 to 12 mm thick layer of absorbent non-woven fibre material of between 150 and 1200 grams per square meter, which layer includes a mixture of viscose fibres and polyester fibres with more viscose than polyester, and of which the linear density of the viscose is between 1.5 and 3 dtex and the linear density of the polyester is between 2 and 3 dtex, wherein the absorbent layer further includes between 7 and 25% chitin fibres mixed or interwoven with the viscose and polyester fibres with the chitin fibres having a linear density between 1.5 and 2.5 dtex.

2. A wound dressing as claimed in claim 1, wherein the layer of absorbent non-woven fibre material comprises two or more thinner layers of absorbent non-woven material needle punched together to form a single layer.

3. A wound dressing as claimed in claim 1, wherein one or both sides of the layer of absorbent material are covered by a non-adherent layer.

4. A wound dressing as claimed in claim 3, wherein the non-adherent layer or layers are heat bonded or laminated to the absorbent layer.

5. A wound dressing as claimed in claim 4, wherein the non-adherent layer or layers are selected from a thin polyurethane or HDPE film.

6. A wound dressing as claimed claim 1, wherein the density is between 150 and 1000 grams per square meter.

7. A wound dressing as claimed in claim 1, wherein the polyester fibre length is between about 30 and 70 mm.

8. A wound dressing as claimed in claim 1, wherein the viscose fibre length is between about 20 and 60 mm.

9. A wound dressing as claimed in claim 1, wherein the chitin fibre length is between 30 and 70 mm.

10. A wound dressing as claimed in claim 2, wherein one or both sides of the layer of absorbent material are covered by a non-adherent layer.

11. A wound dressing as claimed in claim 1, wherein the polyester fibre length is between about 30 and 70 mm and wherein the viscose fibre length is between about 20 and 60 mm.

12. A wound dressing as claimed in claim 11, wherein the chitin fibre length is between 30 and 70 mm.

* * * * *